United States Patent [19]
Nikolic et al.

[11] Patent Number: 5,743,267
[45] Date of Patent: Apr. 28, 1998

[54] SYSTEM AND METHOD TO MONITOR THE HEART OF A PATIENT

[75] Inventors: Serjan D. Nikolic, San Francisco; Gary Feierbach, Belmont, both of Calif.

[73] Assignee: Telecom Medical, Inc., San Francisco, Calif.

[21] Appl. No.: 549,375

[22] Filed: Oct. 27, 1995

Related U.S. Application Data

[63] Continuation-in-part of Ser. No. 545,306, Oct. 19, 1995.

[51] Int. Cl.⁶ .................................................. A61B 5/00
[52] U.S. Cl. .......................... 128/673; 128/691; 128/713; 128/903; 128/687
[58] Field of Search ............................... 128/672, 673, 128/675, 677, 680–683, 687, 691, 713, 740, 903

[56] References Cited

U.S. PATENT DOCUMENTS

| | | | |
|---|---|---|---|
| 4,347,851 | 9/1982 | Jundanian | 128/668 |
| 4,404,974 | 9/1983 | Titus | 128/672 |
| 4,712,562 | 12/1987 | Ohanyon et al. | 128/672 |
| 4,798,211 | 1/1989 | Goor et al. | 128/668 |
| 4,899,752 | 2/1990 | Cohen | 128/672 |
| 5,003,976 | 4/1991 | Alt | 128/672 |
| 5,181,517 | 1/1993 | Hickey | 128/673 |
| 5,337,750 | 8/1994 | Walloch | 128/680 |
| 5,368,040 | 11/1994 | Carney | 128/672 |
| 5,388,586 | 2/1995 | Lee et al. | 128/903 |
| 5,482,049 | 1/1996 | Addiss et al. | 128/903 |
| 5,535,752 | 7/1996 | Halperin et al. | 128/673 |
| 5,551,439 | 9/1996 | Hickey | 128/673 |

FOREIGN PATENT DOCUMENTS

3927990 A1   2/1991   Germany.

*Primary Examiner*—Robert L. Nasser

[57] ABSTRACT

A system and method for monitoring a physiological attribute of a patient is disclosed. The system includes a measuring device to measure an absolute physiological attribute of a patient and to generate an absolute physiological attribute signal. The present invention also includes a processing element to receive the measured absolute physiological attribute signal. The processing element then generates a filtered physiological attribute signal by substantially removing the effects of certain bodily functions from the absolute physiological attribute signal and other artifacts of measurement. The processor also generates a set of parameters derived from the filtered physiological attribute signal which are indicative of the health and condition of the patient.

33 Claims, 4 Drawing Sheets

SYSTEM AND METHOD TO MONITOR THE HEART OF A PATIENT

CROSS REFERENCE TO RELATED APPLICATIONS

This is a continuation-in-part application of pending U.S. patent application Ser. No. 08/545,306, entitled "*System and Method to Measure the Heart Condition of a Patient's Heart*" filed Oct. 19, 1995, and assigned to the assignee of the present application.

BACKGROUND OF THE INVENTION

1. Field of the Invention

The present invention relates to medical devices, and more particularly, to an apparatus and method for measuring an absolute physiological attribute of a patient, generating a filtered physiological attribute signal by substantially removing variations in the measured absolute physiological attribute caused by certain bodily activity of the patient, and generating a set of parameters from the filtered physiological attribute signal which can be evaluated to determine the condition of the patient.

2. Description of the Related Art

With recent advances in both the medical and the microelectronic fields, it is now possible to implant semiconductor devices and other electronic circuitry into the body of a patient. Tiny, but powerful, semiconductor chips can be used to gather information and to measure anyone of a number of physiological attributes of the patient, such as blood pressure, the performance and function of the heart, liver, lungs, brain, and other organs of the body. For example, the circulatory system in humans is responsible for transporting oxygen and other nutrients to the cells of the body. The circulatory system includes a heart, and a network or arteries, capillaries and veins. In a heathy patient the heart pumps blood with a certain pressure and volume to ensure that proper blood circulation in the body is maintained. For the sake of providing background information relative to the present invention, a discussion of the heart and congestive heart disease is provided.

Figure 1:
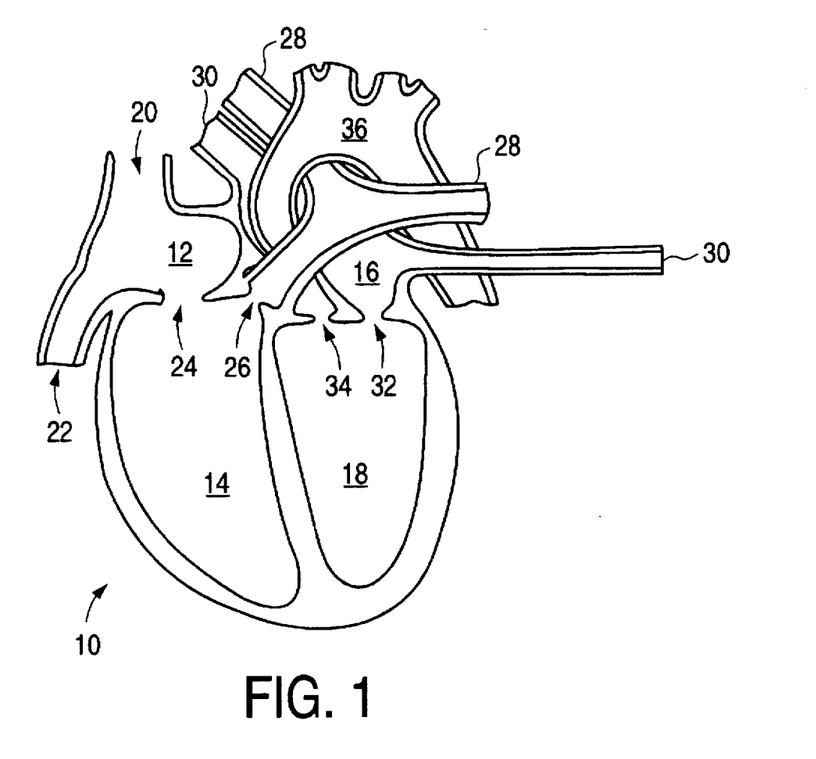
FIG. 1 illustrates a heart of a human patient.

Referring to FIG. 1, a diagram of the human heart is illustrated. The heart 10 includes four chambers, including the right atria 12, the right ventricle 14, the left atria 16, and the left ventricle 18. The right atria 12 receives carbon dioxide laden blood returning from the body through the superior vena cava 20 and inferior vena cava 22. The right ventricle 14 receives blood from the right atria 12 through the triscuspid valve 24 located between the two chambers. The right ventricle 14 pumps blood through the pulmonary valve 26 and into the pulmonary artery 28 which carries the blood to the lungs. After receiving oxygen in the lungs, the blood is returned to the left atria 16 of the heart 10 through pulmonary veins 30. The blood in the left atria 16 passes through the mitral valve 32 and into the left ventricle 18. The blood in the left ventricle 18 is then pumped through the aortic valve 34, into the aorta 36, throughout the body via the network of arteries, capillaries, and finally returned to the heart 10 via the superior vena cava 20 and inferior vena cava 22.

Figure 2:
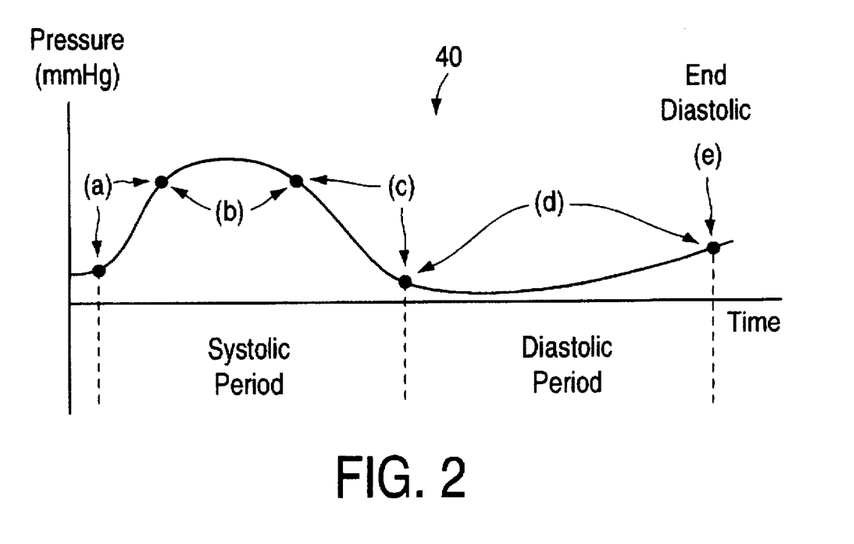
FIG. 2 illustrates a continuous blood pressure signal measured in the right ventricle of a patient.

Referring to FIG. 2, a graph of the continuous blood pressure in the right ventricle 14 during a heart cycle of a patient is shown. The graph 40 plots the pressure P in millimeters of mercury (mmHg) versus time during the heart cycle. The heart cycle is divided into (1) a systolic period and (2) a diastolic period. The systolic period includes the following phases: (a) isovolumic contraction; (b) ejection; and (c) isovolumic relaxation. The diastolic period includes the following: (d) a phase when the right ventricle 14 fills with blood; and (e) the end-diastolic point. The heart cycle shown in graph 40 begins with the end-diastolic phase of the previous cycle.

Congestive heart disease is a condition where the heart fails to adequately contract or relax during the heart cycle. As a consequence, systolic pressures in the heart are lower than normal and diastolic pressures are higher than normal. With the advancement of the disease, systolic pressure gradually decreases, and the diastolic pressure gradually increases. The improper blood pressure in the heart and circulatory system of the patient may cause a number of health problems for the patient. Patients with congestive heart disease are usually afflicted with a malady where congestion occurs in the lungs, liver and other organs of the body. Pulmonary edema, which is congestion in the lungs, is usually asymptomatic, and arises suddenly, without warning. The patent often does not know the edemic condition exists until it progresses to a near fatal state, and the patient suffers from a shortage of breadth due to the congestion in the lungs. Edema is usually treated by admitting the patient into a hospital. The patient is then monitored and treated with medication until the congestion is substantially reduced or eliminated. Congestive heart disease is currently incurable. As the congestive condition of the patient progresses and the heart becomes weaker, bouts of edema tend to increase in intensity and frequency.

One problem of treating patients with congestive heart failure is that it is extremely costly. Each visit to the hospital may last several days and may cost tens of thousands of dollars. With its high degree of incidence, congestive heart disease is an extremely expensive health problem in the United States and other countries. The caring for patients with this disease represents a large percentage of the total expenditures for health care organizations, such as hospitals, health maintenance organizations, and represents a significant financial burden for health insurance companies and federal and local governments. The disease may also create a financial hardship for patients and their families.

U.S. Pat. No. 5,368,040 entitled "*Apparatus and Method for Determining a Plurality of Hemodynamic Variables From a Single, Chronically Implanted Absolute Pressure Sensor*", issued to Carney on Nov. 29, 1994, discloses a radio wave telemetry system for transmitting blood pressure measurement signals generated inside the patient of the body to a receiver located external to the body of the patient. U.S. Pat. No. 5,222,020 entitled "*Acquisition of Atrial Response Process for Pulsating Blood Flow and its Blood Pressure Measuring Method*" issued to Takeda on Jun. 22, 1993, discloses a non-evasive blood pressure measuring apparatus. The apparatus includes a cuff that is wrapped around an artery in a figure, arm or leg for example, a pressure unit, a bleeding unit for inflating the cuff, and a pressure transducer for detecting the cuff's pressure. During operation, the processor is used to receive and process a pressure signal received from the pressure transducer. The processor is then used to display the pressure measurement, along with other parameters, on a CRT or the like. The information may also be sent to a remote location by way of telephone lines. The Applicants are also aware of a number of telemetry systems where information used to control or monitor a cardiac pacemaker is transmitted and received through the skin of a patient. See for example U.S. Pat. No. 5,402,794 entitled "*Method and Apparatus for Heart Transplant Monitoring and Analog Telemetry Calibration*" issued to Wahlstrand on Apr. 4, 1995, U.S. Pat. No. 4,556,063 entitled "Telemetry System for a Medical Device" issued to Thompson on Dec. 3, 1995, U.S. Pat. No. 5,016,634 entitled "Implantable Medical Device with Means For Telemetric Transmission of Data" issued to Vock on May 21, 1991, U.S. Pat. No. 4,867,163 entitled "Cardiac Pacemaker" issued to Schaldach on Sep. 19, 1989 and U.S. Pat. No. 5,157,604 entitled "Heart Rate Monitoring System for Plural Persons Using Radio Telemetry" issued to Axford on Oct. 20, 1992. Lastly, the Applicants are aware of a networked health care system wherein measurements of the passive activities of a patient are sent to a computer via a network. See U.S. Pat. No. 5,410,471 entitled "Network Health Care and Monitoring System" issued to Alyfuku on Apr. 25, 1995.

The Applicants, however, are not aware of system that uses a measurement device to measure an absolute physiological attribute of the body of a patient and to generate an absolute physical attribute signal in response, and a processing element to receive the measured absolute physiological attribute signal and to generate (a) a filtered physiological attribute signal having substantially removed the effects of certain bodily functions and other artifacts of measurement from the absolute physiological attribute signal; and (b) a set of parameters derived from the filtered physiological attribute signal which are indicative of the health and condition of the patient.

SUMMARY OF THE INVENTION

The present invention relates to a system and method for monitoring the condition of a patient. The system includes a measuring device to measure an absolute physiological attribute of a patient and to generate an absolute physiological attribute signal in response. The present invention also includes a processing element to receive the measured absolute physiological attribute signal. The processing element processes and generates a filtered physiological attribute signal by substantially removing the effects of certain bodily functions from the absolute physiological attribute signal and other artifacts of measurement. The processor also generates a set of parameters derived from the filtered physiological attribute signal which are indicative of the health and condition of the patient.

The system further includes a communication element to transmit the set of parameters to a processing station. The processing station receives the set of parameters and processes the information to aid medical personal in diagnosing and treating the patient. In one embodiment, the patient and the processing station are located at different locations. The communication element is capable of transmitting the set of parameters received from the patient to a remote location where the processing station is located, such as in a hospital or a doctor's office. A doctor may monitor a patient from a remote location, diagnose a health related problem, and subscribe a treatment to correct the condition. With the present invention, it is therefore possible to treat the patient sooner than previously possible, and if the condition is corrected, without requiring the patient to visit the doctor's office or admitting the patient into the hospital. The predicament of the patient is therefore improved, and many of the costs associated with treating the patient are eliminated.

The present invention provides numerous advantages. The filtering technique and the set of parameters used to measure the physiological attribute of the patient provides medical personnel with a wealth of information to accurately monitor, diagnose and treat patients with certain chronic diseases and conditions. The present invention provides an efficient, highly accurate and realistic portrayal of the actual physiological attribute of the patient, never before possible with prior art medical instrumentation or techniques.

In one embodiment, the measuring device is used to generate an absolute blood pressure signal indicative of the absolute blood pressure of the patient. The processing element receives and processes the absolute blood pressure signal, and generates (1) a filtered blood pressure signal by substantially removing variations from the absolute blood pressure signal caused by respiratory activity of the patient and other artifacts of measurement; and (2) a set of parameters derived from the filtered blood pressure signal. The set of parameters measure certain aspects of the filtered blood pressure signal which are indicative of the performance and condition of the patient's heart. The communication element transmits the set of parameters to a processing station at a remote location, such as at a hospital or doctor's office. The processing station then processes this information, and presents it to personnel in a user friendly format. The personnel can then conveniently and accurately evaluate the condition of the patient, and subscribe a medical treatment for the patient, if needed. A patient with congestive heart disease can therefore be monitored and treated from a remote location. With early detection of a weakening of the patient's heart for example, a doctor can subscribe a treatment to correct the patient's condition before hospitalization is required.

In alternative embodiments, the present invention could be used to monitor any physiological attribute of a patient. For example, the present invention may be used to monitor the lungs, liver, kidneys, brain, or any other bodily functions and organs.

DESCRIPTION OF THE DRAWINGS

The features and advantages of the present invention will be apparent from the following description in which.

DESCRIPTION OF THE PREFERRED EMBODIMENT

The Applicants have chosen to describe the features and advantages of the present invention in the context of monitoring the blood pressure in the heart of a patient with congestive heart disease. This description, however, should not be construed as limiting, and it will be apparent to those skilled in the art that the present invention may be used to measure and monitor any physiological attribute of the patient.

Figure 3:
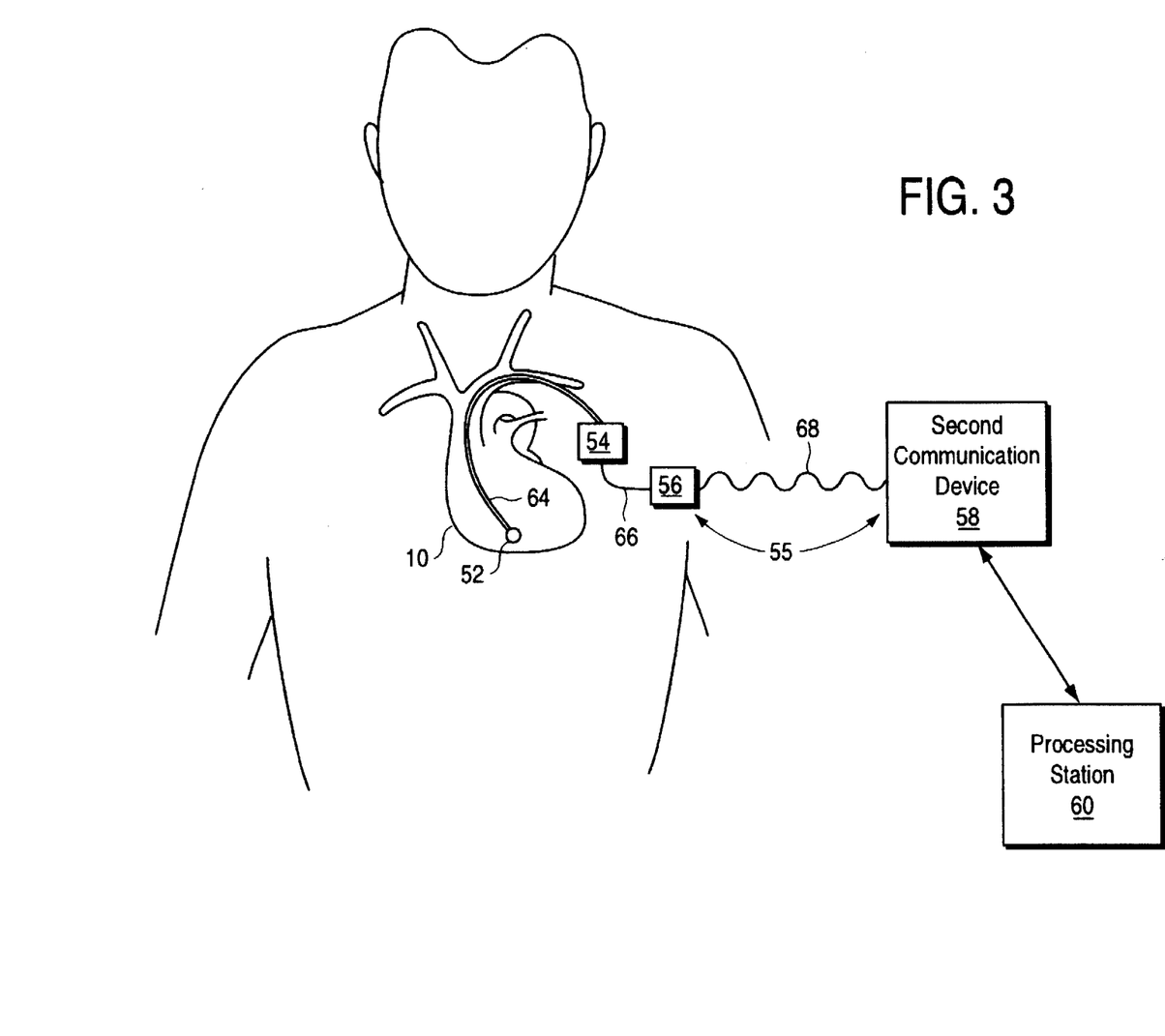
FIG. 3 illustrates a system for measuring the blood pressure in a patient according to the present invention.

Referring to FIG. 3, a system to monitor the heart condition of a patient according to the present invention is shown. The system 50 includes a blood pressure sensor 52, a processing element 54, a communication element 55, including a first communication device 56, a second communication device 58, and a processing station 60. A first interconnect 64 couples the blood pressure sensor 52 and the processing element 54. A second interconnect 66 couples the processing element 54 and the first communication device 56. A link 68 couples the first and second communication devices 56 and 58 through the skin of the patient. The blood pressure sensor 52, the processing element 54, and the first communication device 56 are preferably chronically implanted into the body of the patient. The link 68 between the first communication 56 device and the second communication device 58 is preferably wireless. In one embodiment, the Conifix model number 501112 from the InnoMedica Corporation, Minneapolis, Minn. is used for the interconnect 64 and the interconnect 66.

The blood pressure sensor 52 is implanted in the right ventricle 14 of the heart 10. The blood pressure sensor 52 measures and generates a continuous signal indicative of the absolute blood pressure in the right ventricle 14. The absolute blood pressure is measured relative to a vacuum or zero pressure. In one embodiment, the pressure sensor 52 can be any type of solid state blood pressure transducer, such as model number SPC-320 from the Millar Corporation, Houston, Tex. Such a blood pressure sensor 52 is preferably implanted using a catheter or some other technique. In alternative embedments, the absolute blood pressure can be measured using a number of other techniques, such as by using ultrasound, Doppler, a cuff or some other measuring technique.

The processing element 54 is an electronic component designed to be implanted under the skin of the patient. The processing element 54 processes the absolute blood pressure signal, and generates a filtered blood pressure signal in response. The processing element 54 also analyses the filtered blood pressure signal, and generates a set of parameters indicative of the heart condition of the patient. Each of the parameters measure a particular aspect of the patient's heart cycle which may be used by a doctor to determine the systolic and diastolic function of the heart. In accordance with various embodiments of the present invention, the processing element 54 may include either digital circuitry, analog circuitry, or a combination thereof.

The first communication device 56 and the second communication device 58 of the communication element 55 are designed to communicate through the skin of the patient. The purpose of the first communication device 56 is to transmit the filtered blood pressure signal and the set of parameters generated by the processing element 54 external to the body of the patient. The purpose of the second communication device 58 is to transmit control information to the first communication device 56, which in turn controls the processing element 54. Such information may include "power up" and "power down" signals, signals to instruct the processing element 54 to generate a filtered blood pressure signal and a corresponding set of parameters, timing signals to instruct the processing element 54 to generate the same at a specific time, or at specific intervals of time, test or calibration signals, and other control related information. The second communication device 58 is also use to temporarily store filtered blood pressure signals and their corresponding set of parameters received from the first communication device 56. The second communication device stores this information until it is transmitted to the processing station 60. The second communication device can also be used to receive information from the processing station 60, and to up-load this information to the processing element 54 via the first communication device 56. This feature permits new functionally and processing capabilities to be added to the processing element 54 after it has been implanted into the body of the patient.

A number of communication mediums may be used to establish the link 68 between the first communication device 56 and the second communication device 58. The link 68 may be radio waves. See the transdermal telemetry system that is described in the above-mentioned U.S. Pat. No. 5,368,040 issued to Carney, and incorporated by reference herein. The link 68 may rely on light waves or pulses. See U.S. Pat. No. 5,387,259, entitled "*Optical Transdermal Linking Method for Transmitting Power and a First Power Stream While Receiving a Second Data Stream*", issued on Feb. 7, 1995 to Davidson, and incorporated by reference herein. The link 68 can also be a hard-wired port implanted through the skin of the patient. With this embodiment, the second communication device 58 may be "plugged" into the port when communication between the first communication device 56 and second communication device 58 is desired. The link 68 can also be acoustic. With this embodiment, both the first communication device 56 and the second communication device 58 are capable of transmitting, receiving and decoding acoustic audio signals through the skin of the patient.

In accordance with various embodiments of the invention, the processing station 60 may be located in a number of different places. In one embodiment, the processor station 60 may be located in close proximity to the patient, such as in the home of the patient, or in a nursing home where the patient is residing. In another embodiment, the processing station 60 may be located in a remote location relative to the patient. For example, the patient is located at home, and the processing station 60 is located in a hospital or doctor's office. The patient is then required to either (1) visit the hospital or a doctor's office to directly down-load filtered blood pressure signals and related sets of parameters to the processing station 60; or (2) an assistant can bring the second communication device 58 storing such information to the processing station 60. In yet another embodiment, the second communication device 58 has the ability to transmit filtered blood pressure signals and the corresponding sets of parameters to the processor station 60 from a remote location. For example, the second communication device 58 may contain a modem for transmitting the stored information to the remote processing station 60 by way of the telephone lines. In another example, the second communication device 58 may be a home computer that is capable of transmitting the filtered blood pressure signals and related parameters to the processing station 60 via the Internet, or some other computer network. In yet another example, the second communication device 58 is a radio transmitter/receiver that is capable of transmitting and receiving information to and from the processing station 60 using a wireless communication protocol. Regardless of the transmission medium, these embodiments all have the advantage of permitting the patient to be monitored by a doctor from a remote location, without requiring the patient to visit the doctor's office or be admitted into the hospital.

The processing station 60 is a computer, such as a personal computer, work station, mini-computer or a main frame. The processing station 60 is programmed to perform data processing on the information received from the patient. For example, the processing station 60 is programmed to create a specific record for each patient. Each record may include previously measured filtered blood pressure signals, their corresponding set of parameters, and other medical information related to the patient. The processing station 60 is also programmed to present the filtered blood pressure signals and parameters in a user friendly format. A doctor may direct the processing station 60 to compile and display a number of current and previous filtered blood pressure signals and their corresponding set of parameters, sampled over a period of time. The compiled information can then be used to interpret certain trends in the patient's heart condition over time. For example, a plot illustrating a steady drop in a patients maximum systolic pressure over a defined period of time may indicate a weakening of the patient's heart. A doctor can then prescribe a medical treatment to correct the problem, before the patient progresses into a more severe condition requiring admission into a hospital. In summary, the processing station 60 may perform any type of data processing on the received information that may help medical personal monitor, diagnose and treat a congestive heart condition of a patient.

The absolute blood pressure in the right ventricle 14 is affected by the respiratory activity of the patient. The normal increase and decrease of pressure in the chest and lungs, caused by breathing, typically causes a corresponding increase or decrease of blood pressure in the heart. Therefore, analyzing an absolute blood pressure signal may lead to an incorrect diagnosis because it is difficult to determine if pressure changes are due to problems related to congestive heart disease, or the normal respiratory activity of the patient. The Applicant has therefore devised a way to filter and substantially remove variations in the absolute blood pressure signal caused by the respiratory activity of the patient.

Figure 4:
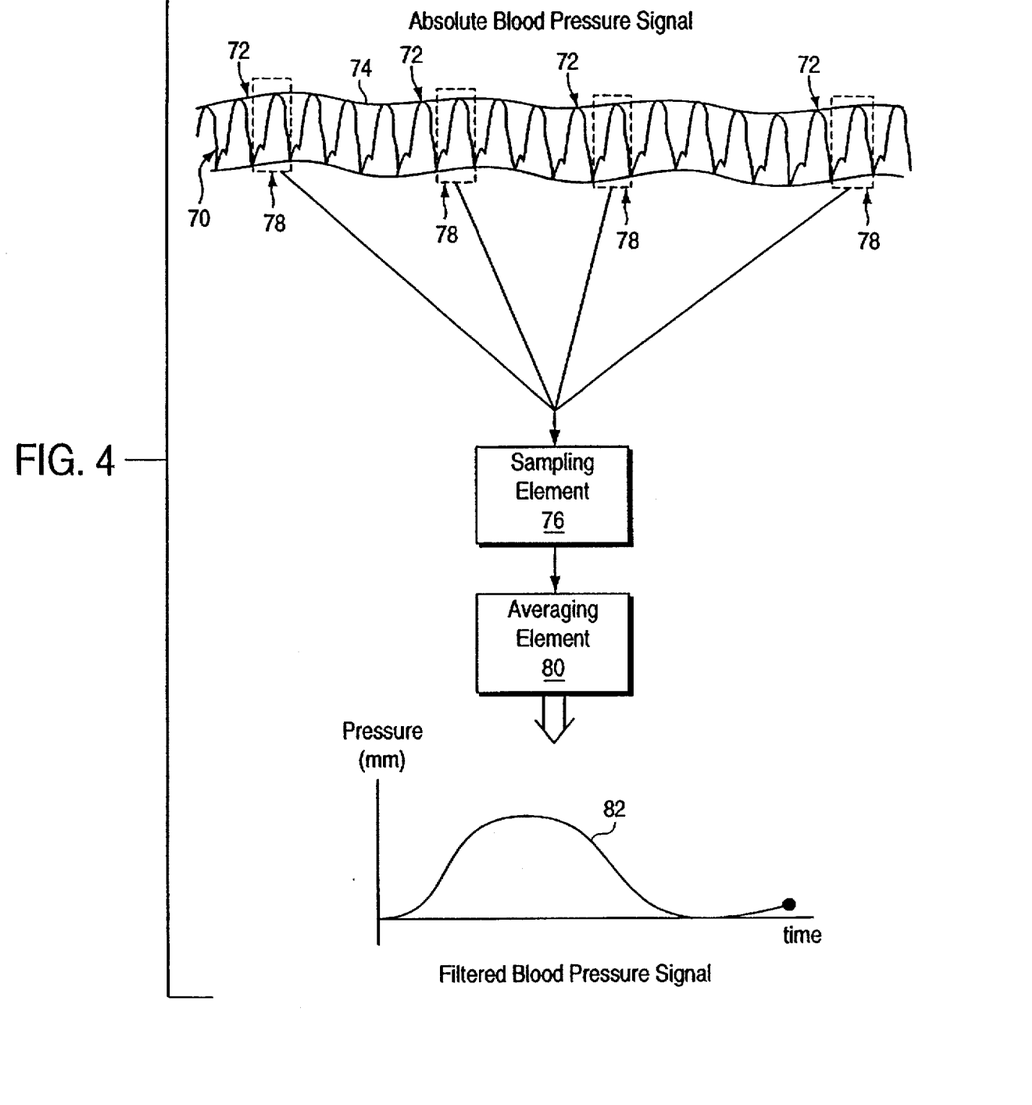
FIG. 4 illustrates the steps of generating a filtered blood pressure signal from an absolute blood pressure signal according to the present invention.

Referring to FIG. 4, an illustration of the steps required to generate a filtered blood pressure signal from an absolute blood pressure signal according to the present invention is shown. The figure illustrates a continuous absolute blood pressure signal 70 including a series of heart cycles as generated by the blood pressure sensor 52. The absolute blood pressure signal 70 is characterized by a number of peaks 72 and valleys 74 caused by the respiratory cycles of the patient. A sampling element 76, contained in the processing element 54, samples a selected heart cycles 78 during each of the respiratory cycles. The samples are preferably taken at the same phase in each respiratory cycle. The sampled heart cycles 78 are then provided to an averaging element 80, also contained in the processing element 54. The averaging element 80 averages the sampled heart cycles 78, and generates a filtered blood pressure signal 82. It should be noted that the number of sampled heart cycles 78 per respiratory cycle, the phase of the sampled heart cycles 78 in the respiratory cycle, and the number of respiratory cycles sampled, are all design choices. The Applicant recommends that one heart cycle sample at the peak exhalation period, or the peak inhalation period, of three or four consecutive respiratory cycles be used to generate the filtered blood pressure signal 82.

A number of benefits are realized by generating the filtered blood pressure signal 82. Most significantly, the filtering of the absolute blood pressure signal 70 removes most of the variants caused by the respiratory activity of the patient and other artifacts of measurement. The filtered blood pressure signal 82 therefore offers a more accurate indicator of the performance and condition of the patient's heart. The filtered blood pressure signal is also analyzed using a predefined set of parameters. Each one of the set of parameters is indicative of the ability and efficiency of the patient's heart, and quality of the patient's heart cycle. These parameters provide an efficient, highly accurate and realistic measurement of the actual heart condition of the patient.

Figure 5:
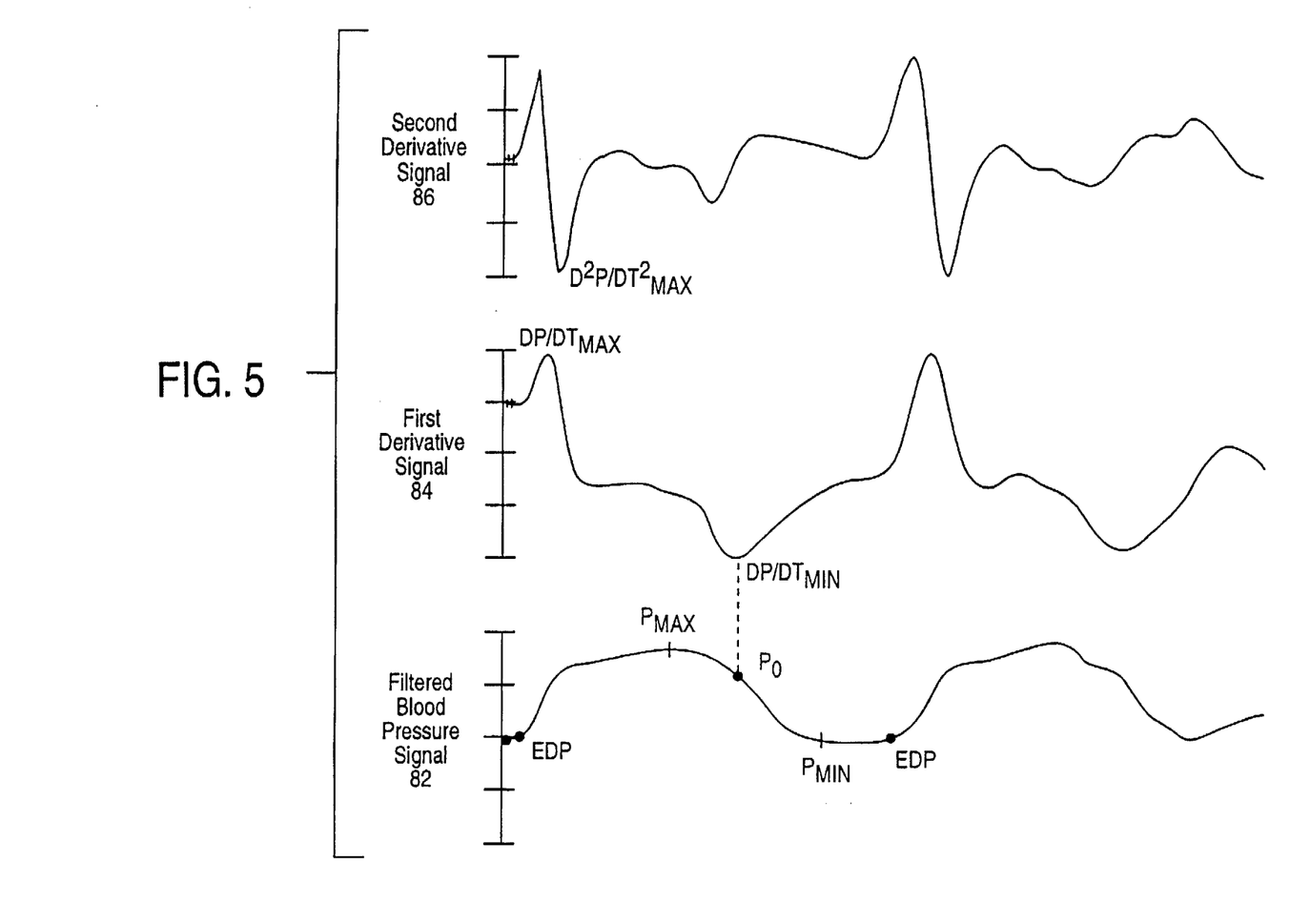
FIG. 5 illustrates the measured parameters from the filtered blood pressure signal, a first derivative signal, and a second derivative signal of the filtered blood pressure signal in accordance with the present invention.

Referring to FIG. 5, a plot illustrating the filtered blood signal 82, a first derivative signal 84, and a second derivative 86 of the filtered blood pressure signal 82 is shown. The set of parameters are derived from the filtered blood pressure signal 82; the first derivative signal 84 and the second derivative signal 86. Each of the set of parameters are calculated in the processing element 54 after the filtered blood pressure signal has been generated.

In one embodiment, the processor element 54 includes an analog-to-digital (A/D) converter to sample and digitize the absolute blood pressure signal 70, and a microcontroller to filter the absolute blood pressure signal and to generate the set of parameters, and a read only memory (ROM) for storing the microcode used to control the microcontroller. One type of microcontroller that can be used with the present invention is the PIC 16C7X made by the Microchip Corporation, Chandler, Ariz. The microcontroller generates the filtered blood pressure signal 82 by storing the sampled and digitized absolute blood pressure signal from the A/D converter over a period of three or more respiratory cycles. A heart cycle 78 at the same phase of each of the three or more respiratory cycles is then selected, for example at either the peak inhalation phase or the peak exhalation phase. A base heart cycle is then selected among one of the sampled heart cycles 73. The sampled heart cycles are then interpolated to match the wave form time scale of the base heart cycle so that all sampled heart cycles have the same number of time divisions. The endpoints of the sampled heart cycles 78 are also interpolated since it is unlikely that the sampled heart cycles will all begin and end at the same pressures due to the granularity of the sampling in time. The selected heart cycles 78 are then averaged pointwise with the base heart cycle. Once the filtered blood pressure signal 82 is derived, the microcontroller performs an (n) point differential least-squares fit convolution on the filtered blood pressure signal 82 to obtain the first derivative signal 84, and then repeats this process on the first derivative signal 84 to obtain the second derivative signal 36. The microcontroller then calculates the set of parameters from the equations provided below. In another alternative embodiment, an analog computer may be used to filter the absolute blood pressure signal to generate the set of parameters.

The set of parameters include the following measurements:

(1) dP/dtMAX—This parameter is a measure of the maximum pressure time derivative derived from the signal 84. It is an indicator of the peak pressure increase in the right ventricle 14 during isovolumic contraction. This parameter is related to the contractile ability of the right ventricle 14. The larger the amplitude of dP/dtMAX, the better the heart contraction.

(2) Normalized dP/dtMAX (NdP/dtMAX)—NdP/dtMAX is a useful index of systolic function because it is less dependent on the absolute pressure measurement in the right ventricle 14. This parameter has the same meaning as dP/dtMAX. The larger the amplitude of NdP/dtMAX, the better the heart condition.

(3) Time to dP/dtMAX$_t$—This parameter is a measure of the time to dP/dtMAX. This parameter is related to the contractile properties of the right ventricle 14. The shorter the time to dP/dtMAX$_t$, the better the systolic function. This parameter is not sensitive to absolute pressure, but it is sensitive to the heart rate. Therefore, this parameter is also provided in a normalized form.

(4) Normalized time to dP/dtMAX$_t$ (NdP/dtMAX$_t$)—This parameter is normalized to the heart rate in accordance with the equation NdP/dtMAX$_t$=(120/HR −0.49).

(5) $d^2$P/dtMIN—This parameter is a measure of the first minimum of the second derivative signal 86.

(6) $d^2P/dtMIN@(5\%)$—This parameter is a measure of the pressure at (5%) of $d^2P/dtMIN$ at the down slope of the second derivative.

(7) PMAX—This parameter is a measure of the peak systolic ventricular pressure derived from signal 82. The peak pressure is a measure of the ability of the right ventricle 14 to generate blood pressure. It is a useful indicator of the overall hemodynamic status of the patient.

(8) dP/dtMIN—This parameter is a measure of the minimum of the first derivative signal 84. It represents the peak rate of pressure decrease during isovolumic relaxation.

(9) $dP/dtMIN_t$—This parameter is a measure of the time to dP/dtMIN. It is a measure of the relaxation properties of the right ventricle 14.

(10) Systolic Time—This parameter measures the difference between $(dP/dtMIN_t-dP/dtPMAX_t)$.

(11) PMIN—This parameter is a measure of the minimum ventricular pressure taken from the filtered signal 82. It is a useful indicator of the ability of the right ventricle 14 to relax.

(12) PO—This parameter is a measure of the pressure at the time of dP/dtMIN.

(13) Time constant of isovolumic pressure decay tau ($\tau$). The constant of isovolumic pressure decay ($\tau$) is calculated by using a least squares fit or some other mathematical relaxation algorithm for a number (m) of points $P_1$ through $P_m$ sampled during the iso-relaxation phase of the filtered blood pressure signal 82. In accordance with the least squares fit algorithm, the heart relaxation time constant ($\tau$) is derived by systematically varying the coefficients (A) and (B) in the equation $P=Ae^{-t/\tau}+B$ for each sampled pressure point $P_1$ through $P_m$ to achieve an optimal fit for the sampled data points. This parameter is indicative of the process of relaxation.

(14) PINF—This parameter is a measure of the asymptote of the isovolumic relaxation pressure exponential. This asymptote allows the estimate of completeness of relaxation. Tau and and PINF are determined from the exponential fit of the form $P=(PO-PINF)e^{(-t/\tau)}+PINF$. In accordance with the least squares fit algorithm, the tau ($\tau$) and PINF are determined with the best fit of the sampling points between PO and PMIN+the pressure at a predetermined number of sample points prior to PMIN. In one embodiment, the predetermined number is ten.

(15) MDP—The mean diastolic pressure measurement is calculated by sampling a number (n) of pressure points $P_1$, $P_2$, through $P_n$ during the diastolic period of the filtered blood pressure signal 82. The mean diastolic pressure (MDP) measurement is then calculated from equation $(MDP=P_1+P_2+\ldots P_n/n)$.

(16) EDP—This parameter is a measure of the pressure of the filtered blood pressure signal 82 at a time corresponding to a predetermined percentage of dP/dtMAX on the upstroke of dP/dt. In one embodiment, the predetermined percentage is (5%). The end diastolic pressure indicates passive elastic properties of the ventricle. Combined with the constant of isovolumic pressure decay ($\tau$) and PINF, this parameter can provide an insight into the changes in the active process of relaxation and passive elastic properties of the right ventricle 14.

(17) $EDP_t$—This parameter is a measure of the time to end diastolic pressure.

(18) Diastolic Time—This parameter measures the difference between $(EDP_t-dP/dtMIN_t)$.

(19) Heart Rate (HR)—This parameter is determined by $60/EDP_t$.

The above parameters provide a highly accurate representation of the condition and quality of the heart of a patient. With proper use, a doctor can accurately monitor the condition of a patient's heart. For example, a patient can be directed to sample and generate a set of parameters at specified time intervals subscribed by a doctor. This information can then be transmitted to the doctor and analyzed at a remote location. By comparing the relative differences of a current set of parameters with previous sets of parameters, the condition of the patient's heart can be ascertained.

While the present invention has been described in relationship to the embodiments described in the accompanying specification, other alternatives, embodiments and modifications will be apparent to one skilled in the art. For example, the blood pressure sensor 52 can be located in any one of the chambers of the heart, the lungs, an artery or vein, or any other location in the circulatory system. In yet another alternative embodiment, the blood pressure sensor 52 and the processing element 54 can be integrated into a single unit that is implanted into the heart of the patient. In yet another embodiment, the internal communication device can be coupled directly to the pressure sensor. The internal communication device would receive and transmit the absolute blood pressure signal external to the body of the patient, using for example RF signals. The absolute blood pressure signal would then be processed by a processing element, external to the body of the patient. In yet another embodiment, the physiological attribute of the patient can be measured external to the patient, using some non-evasive technique. The generation and processing of filtered physiological signal and the set of parameters would all take place external to the body of the patient in this embodiment. The present invention can also be used to monitor heart transplant patients, or patients with faulty heart valves.

The present invention could be used to measure and monitor any physiological attribute of a patient. For example, the present invention may be used to monitor any organ in the body, including, but not limited to the lungs, liver, kidneys, brain, or any other organ. The present invention could similarly monitor anyone of a number of systems in the body, including but not limited to, the digestive system, the circulatory system, the reproductive system, the nervous system, etc. The present invention could also be used to monitor chemical and hormonal activity in the body. For the sake of brevity, a detailed description of the actual filtering techniques, or the set of parameters needed to monitor a patient for each of these physiological attributes is not provided. However, it is sufficient to say that regardless of the physiological attribute, the process of monitoring the patient includes the following steps: generating an absolute signal indicative of the absolute physiological attribute of the patient; generating a filtered signal from the absolute signal by removing variations caused by bodily functions that may alter or affect the absolute signal; generating a set of parameters indicative of the patients health from the filtered signal; and analyzing the set of parameters to determine the health and condition of the patient with respect to the measured physiological attribute. It is intended that the specification be only exemplary, and that the true scope and spirit of the invention be indicated by the following claims.

What is claimed is:

1. A system used to monitor a patient's heart, the system comprising:
   a measuring device configured to measure the absolute blood pressure of the patient and to generate an absolute blood pressure signal; and
   a processing element configured to be coupled to receive the absolute blood pressure signal, the processing element being further configured to generate a filtered blood pressure signal from the absolute blood pressure signal by substantially removing variations from the absolute blood pressure signal caused by the respiratory activity of the patient, the processing element further including:
      a filtering element further including a sampling element configured to sample the absolute blood pressure signal during a plurality of selected heart cycles that occur over a course of a plurality of respiratory cycles of the patient, the plurality of selected heart cycles being selected at approximately the same phase during each of the plurality of respiratory cycles respectively;
      an averaging element configured to generate the filtered blood pressure signal by averaging the absolute blood pressure signal measured during the plurality of selected heart cycles; and
   a computation element configured to generate a set of parameters derived from the filtered blood pressure signal which are indicative of the condition of the patient.

2. The system of claim 1, further comprising:
   a processing station, coupled to receive the set of parameters, and configured to process the set of parameters to monitor the patient; and
   a communication element configured to communicate the set of parameters from the processing element to the processing station.

3. The system of clam 2, wherein the communication element includes a first communication device configured to be implanted into the body of the patient and coupled to the processing element, and a second communication device configured to be located external to the body of the patient.

4. The system of claim 3, wherein the first communication device and the second communication device communicate through a communication medium, the communication medium selected from one of the following group of communication mediums, including: radio waves, light waves, acoustic sound waves, or a hard wired port coupled between the first communication device and the second communication device.

5. The system of claim 2, wherein the communication element and the processing station communicate through a transmission medium, the transmission medium selected from one of the following group of transmission mediums, including: telephone lines, radio waves, light waves, acoustic sound waves, a computer network, or a wired interconnect coupled between the communication element and the processing station.

6. The system of claim 2, wherein the processing station is configured to be located at a position remote from the patient, and the processing station is further configured to process the set of parameters to aid personal in diagnosing the patient from the remote location.

7. The system of claim 2, wherein the processing station is further configured to maintain a record containing information related to the patient, the record containing a plurality of the sets of parameters generated at specific points of time respectively.

8. The system of claim 1, wherein the measuring device is a pressure transducer configured to be implanted into the heart of the patient.

9. The system of claim 1, wherein the selected phase is an end exhalation phase of each of the plurality of respiratory cycles.

10. The system of claim 1, wherein the selected phase is an end inhalation phase of each of the plurality of respiratory cycles.

11. The system of claim 1, wherein the set of parameters are selected from the following group of parameters: (a) a peak systolic pressure measurement of the filtered blood pressure signal; (b) a minimum diastolic pressure measurement of the filtered blood pressure signal; (c) a mean diastolic pressure measurement of the filtered blood pressure signal; (d) a time constant of isovolumic pressure decay indicative of the rate at which the heart of the patient relaxes; (e) a contraction signal indicative of the ability of the heart of the patient to contract; (e) a contraction signal derived by determining a change in blood pressure over time during an isovolumic contraction phase of the filtered blood pressure signal; (f) a maximum pressure time derivative signal; (g) a normalized maximum pressure time derivative signal; (h) a time to the maximum pressure time derivative signal; (i) a normalized time to the maximum pressure time derivative signal; (j) a relaxation signal indicative of the ability of the heart of the patient to relax by calculating a change in pressure over time during an isovolumic relaxation phase of the filtered blood pressure signal; (k) a minimum pressure time derivative; (l) a time to the minimum pressure time derivative; (m) the pressure of the filtered blood pressure signal at the time to the minimum pressure time derivative; (n) a minimum of the second derivative; (o) the blood pressure at a predetermined point in the down slope of the second derivative of the filtered blood signal; (p) end diastolic pressure signal; (q) a time to the end diastolic pressure signal; (r) a time measurement of a diastolic period of the filtered blood pressure signal; (s) a measure of an asymptote of isovolumic relaxation pressure exponential derived from the filtered blood pressure signal; and (t) a signal indicative of the heart rate of the patient.

12. The system of claim 1, wherein the processing element is an implantable device designed to be implanted into the body of the patient and includes circuitry configured to process the absolute physiological attribute signal and to generate the set of parameters.

13. The system of claim 7, wherein the processing station further comprises a processing unit configured to process the plurality of sets of parameters and to generate a display indicative of changes in the physiological attribute of the patient over the specific points in time.

14. The system of claim 1, wherein the measuring device is configured to be embedded into the patient.

15. The system of claim 1, wherein the measuring device is configured to be located external to the body of the patient and measures the absolute blood pressure of the patient using a non-invasive technique.

16. The system of claim 1, wherein the processing element is configured to be located external to the body of the patient.

17. The system of claim 1, wherein the processing element is configured to be implanted into the body of the patient.

18. A method to monitor a patient's heart, the method comprising the steps of:

measuring the absolute blood pressure of the patient;

generating an absolute blood pressure signal indicative of the absolute blood pressure of the patient;

generating a filtered blood pressure signal from the absolute blood pressure signal by substantially removing variations from the absolute blood pressure signal caused by the respiratory activity of the patient;

generating a set of parameters derived from the filtered blood pressure signal which are indicative of the condition of the patient's heart;

transmitting the set of parameters to a processing station;

analyzing the set of parameters to monitor the condition of the patient's heart;

the step of generating the filtered blood pressure signal further comprising the steps of:

sampling the absolute blood pressure signal during a plurality of selected heart cycles that occur over the course of a plurality of respiratory cycles of the patient, the selected heart cycles being selected at a approximately the same phase of each of the plurality of respiratory cycles;

generating a plurality of sampled blood pressure signals during the plurality of selected heart cycles;

averaging the plurality of sampled blood pressure signals; and generating the filtered blood pressure signal from the averaged blood pressure signal.

19. The method of claim 18, wherein the selected phase is an end exhalation phase of each of the plurality of respiratory cycles.

20. The method of claim 18, wherein the selected phase is an end inhalation phase of each of the plurality of respiratory cycles.

21. The method of claim 18, wherein the transmitting step further includes the step of communicating the set of parameters from a first communication device located internal to the body of the patient to a second communication device located external to the patient of the body.

22. The method of claim 21, wherein the communication step includes the step of communicating between the first communication device and the second communication device through a communication medium, the communication medium selected from one of the following group of communication mediums, including: radio waves, light waves, acoustic sound waves, or a wire interconnect coupled between the first communication device and the second communication device.

23. The method of claim 18, wherein the transmitting step further includes the step of communicating the set of parameters to the processing station through a communication medium, the communication medium selected from one of the following group of communication mediums, including: telephone lines, radio waves, light waves, acoustic sound waves, a computer network, or a wire interconnect.

24. The system of claim 18, wherein the step of analyzing the set of parameters occurs at a position remote from the patient.

25. A method of monitoring the heart of a patient, comprising the steps of:

sampling the blood pressure of the patient over a first series of respiratory cycles of the patient during a first period in time;

generating a first absolute blood pressure signal over the first series of respiratory cycles;

generating a first filtered blood pressure signal by substantially removing variations in the first absolute blood pressure signal caused by respiratory activity of the patient during the first series of respiratory cycles;

the step of generating the first filtered blood pressure signal further comprising the steps of:

sampling the first absolute blood pressure signal during a first plurality of selected heart cycles that occur over the course of the first plurality of respiratory cycles, the selected first plurality of heart cycles being selected at approximately the same phase of each of the first plurality of respiratory cycles;

generating a first plurality of sampled blood pressure signals from the first plurality of selected heart cycles:

averaging the first plurality of sampled blood pressure signals;

generating the first filtered blood pressure signal from the averaged first plurality of sampled blood pressure signals;

generating a first set of parameters from the first filtered blood pressure signal, the first set of parameters indicative of the condition of the heart of the patient during the first period in time; and analyzing the first set of parameters.

26. The method of claim 25, further comprising the steps of:

sampling the blood pressure of the patient over a second series of respiratory cycles of the patient during a second period of time;

generating a second absolute blood pressure signal over the second series of respiratory cycles;

generating a second filtered blood pressure signal by substantially removing variations in the second absolute blood pressure signal caused by the respiratory activity of the patient during the second series of respiratory cycles;

the step of generating the second filtered blood pressure signal further comprising the steps of:

sampling the second absolute blood pressure signal during a second plurality of selected heart cycles that occur over the course of the second plurality of respiratory cycles, the second plurality of selected heart cycles being selected at approximately the same phase of each of the second plurality of respiratory cycles;

generating a plurality of second sampled blood pressure signals from the second plurality of selected heart cycles:

averaging the second plurality of sampled blood pressure signals;

generating a second filtered blood pressure signal from the second averaged plurality of sampled blood pressure signals;

generating a second set of parameters from the second filtered blood pressure signal, the second set of parameters indicative of the condition of the heart of the patient during the second period in time; and analyzing the second set of parameters.

27. The method of claim 26, further comprising the steps of comparing the first set of parameters and the second set of parameters;

ascertaining the relative difference between the first set of parameters and the second set of parameters; and monitoring the condition of the heart of the patient based on the relative difference between the first set of parameters and the second set of parameters.

28. The method of claim 27, further comprising the step of subscribing a medical treatment for the patient based on the monitoring step.

29. The method of claim 25, further comprising the step of communicating the first set of parameters to a location remote from the patient so that the heart condition of the patient can be monitored from the remote location.

30. The method of claim 25, wherein the step of generating the first set of parameters includes the step of generating at least one of the following group of parameters: (a) a peak systolic pressure measurement of the filtered blood pressure signal; (b) a minimum diastolic pressure measurement of the filtered blood pressure signal; (c) a mean diastolic pressure measurement of the filtered blood pressure signal; (d) a time constant of isovolumic pressure decay indicative of the rate at which the heart of the patient relaxes; (e) a contraction signal indicative of the ability of the heart of the patient to contract; (e) a contraction signal derived by determining a change in blood pressure over time during an isovolumic contraction phase of the filtered blood pressure signal; (f) a maximum pressure time derivative signal; (g) a normalized maximum pressure time derivative signal; (h) a time to the maximum pressure time derivative signal; (i) a normalized time to the maximum pressure time derivative signal; (j) a relaxation signal indicative of the ability of the heart of the patient to relax by calculating a change in pressure over time during an isovolumic relaxation phase of the filtered blood pressure signal; (k) a minimum pressure time derivative; (l) a time to the minimum pressure time derivative; (m) the pressure of the filtered blood pressure signal at the time to the minimum pressure time derivative; (n) a minimum of the second derivative; (o) the blood pressure at a predetermined point in the down slope of the second derivative of the filtered blood signal; (p) end diastolic pressure signal; (q) a time to the end diastolic pressure signal; (r) a time measurement of a diastolic period of the filtered blood pressure signal; (s) a measure of an asymptote of isovolumic relaxation pressure exponential derived from the filtered blood pressure signal; and (t) a signal indicative of the heart rate of the patient.

31. The method of claim 25, wherein the step of sampling the blood pressure of the patient further includes the step of implanting a blood pressure sensor into the heart of the patient.

32. The method of claim 25, wherein the step of generating the first set of parameters comprises the step of providing the patient with a processing element configured to receive the first absolute blood pressure signal, configured to generate the first filtered blood pressure signal, and further configured to generate the first set of parameters.

33. The method of claim 25, further comprising the step of providing the patient with a communication element so that the patient can communicate the first set of parameters to a remote location where the analysis step takes place.

* * * * *